(12) United States Patent
Cardonna et al.

(10) Patent No.: US 9,975,492 B2
(45) Date of Patent: May 22, 2018

(54) BOTTLE HOLDER

(71) Applicant: SURE-LOK INTERNATIONAL, LLC

(72) Inventors: Edgardo Cardonna, Ft. Lauderdale, FL (US); Jason A. Bandi, Hellertown, PA (US)

(73) Assignee: Sure-Lok International, LLC, Bethlehem, PA (US)

( * ) Notice: Subject to any disclaimer, the term of this patent is extended or adjusted under 35 U.S.C. 154(b) by 392 days.

(21) Appl. No.: 13/918,545

(22) Filed: Jun. 14, 2013

(65) Prior Publication Data
US 2013/0334269 A1 Dec. 19, 2013

Related U.S. Application Data

(60) Provisional application No. 61/660,647, filed on Jun. 15, 2012.

(51) Int. Cl.
| | |
|---|---|
| *B60R 9/00* | (2006.01) |
| *A45F 5/00* | (2006.01) |
| *B60R 11/00* | (2006.01) |
| *B60R 7/08* | (2006.01) |
| *B60N 3/10* | (2006.01) |
| *F17C 13/08* | (2006.01) |

(Continued)

(52) U.S. Cl.
CPC ............... *B60R 7/08* (2013.01); *B60N 3/106* (2013.01); *B60R 11/00* (2013.01); *F17C 13/084* (2013.01); *A61G 3/001* (2013.01); *A61M 16/10* (2013.01); *A61M 2202/0208* (2013.01); *A61M 2209/082* (2013.01); *B60R 2011/0071* (2013.01); *B60R 2011/0084* (2013.01)

(58) Field of Classification Search
CPC ... B60R 7/08; B60R 11/00; B60R 2011/0084; B60R 2011/0071; F17C 13/084; B60N 3/106; A61M 2209/082; A61M 2202/0208; A61M 16/10; A61G 3/001
USPC ........ 224/402, 554, 148.5, 148.7; 248/311.2; 410/104, 94
See application file for complete search history.

(56) References Cited

U.S. PATENT DOCUMENTS 2,532,244 A * 11/1950 Pasmore ........................ 220/278
2,754,078 A * 7/1956 Koger et al. ............... 248/311.2

(Continued)

*Primary Examiner* — Nathan J Newhouse
*Assistant Examiner* — Lester L Vanterpool
(74) *Attorney, Agent, or Firm* — Daniel A. Tallitsch; Baker McKenzie LLP

(57) ABSTRACT

A securement system for portable bottles, intended for use in a vehicle, is disclosed and claimed herein. In one particular embodiment, the securement system is constructed from a vertical stanchion. Disposed about the periphery, on four sides, are four vertically oriented mounting channels. A top bottle holder and a bottom bottle holder are installed in a selected mounting channel. At least the top bottle holder can be adjusted vertically to accommodate bottles with various heights. The bottom bottle holder includes a platform for supporting the bottle, and both the top and bottom holder include a cradle that receives a side of the bottle. Both the top bottle holder and bottom bottle holder include releasable, hook and loop straps to hold the bottle flush and secure against the cradles. The base of the stanchion includes features for securing the stanchion in a convention L-Track, of the type typically found in transit vehicles.

18 Claims, 7 Drawing Sheets

(51) Int. Cl.
*A61G 3/00* (2006.01)
*A61M 16/10* (2006.01)

(56) References Cited

U.S. PATENT DOCUMENTS

| | | | | |
|---|---|---|---|---|
| 2,987,231 A * | 6/1961 | Lewis | ............... | B44D 3/14 |
| | | | | 224/148.4 |
| 3,224,644 A * | 12/1965 | Davis | ............... | 222/162 |
| 3,253,786 A * | 5/1966 | Parmelee | ............... | 239/284.1 |
| 4,655,425 A * | 4/1987 | Wallace | ............... | B60N 3/18 |
| | | | | 248/308 |
| 4,830,247 A * | 5/1989 | Banks | ............... | 224/666 |
| 4,850,769 A * | 7/1989 | Matthews | ............... | B60P 7/0815 |
| | | | | 410/105 |
| 4,951,910 A * | 8/1990 | March | ............... | 248/311.2 |
| 5,042,770 A * | 8/1991 | Louthan | ............... | 248/311.2 |
| 5,232,137 A * | 8/1993 | Devine | ............... | A45F 5/02 |
| | | | | 222/175 |
| 5,249,770 A * | 10/1993 | Louthan | ............... | A47K 1/09 |
| | | | | 248/205.2 |
| 6,045,017 A * | 4/2000 | Connell | ............... | 224/148.7 |
| 6,098,860 A * | 8/2000 | Phillips | ............... | B60N 3/103 |
| | | | | 224/482 |
| 6,557,738 B1 * | 5/2003 | Meintzer | ............... | 224/148.7 |
| 6,769,659 B1 * | 8/2004 | Martello | ............... | B60N 3/103 |
| | | | | 248/154 |
| 6,883,766 B1 | 4/2005 | Zaiylek et al. | | |
| 7,591,498 B2 * | 9/2009 | Busha | ............... | B60N 2/4686 |
| | | | | 224/281 |
| 7,637,404 B1 * | 12/2009 | Stepanova | ............... | B60R 7/085 |
| | | | | 224/275 |
| 7,963,597 B2 * | 6/2011 | Bostrom | ............... | A62B 9/04 |
| | | | | 248/313 |
| 7,980,798 B1 * | 7/2011 | Kuehn | ............... | B60P 7/0815 |
| | | | | 410/104 |
| 2004/0217247 A1 * | 11/2004 | Andrews | ............... | B60N 3/103 |
| | | | | 248/311.2 |
| 2005/0017145 A1 * | 1/2005 | Kent-Fawkes | ............... | 248/311.2 |
| 2006/0239790 A1 | 10/2006 | Earle et al. | | |
| 2008/0296325 A1 * | 12/2008 | Tepper | ............... | A45F 5/00 |
| | | | | 224/148.6 |
| 2010/0213151 A1 | 8/2010 | Theesefeld et al. | | |

* cited by examiner

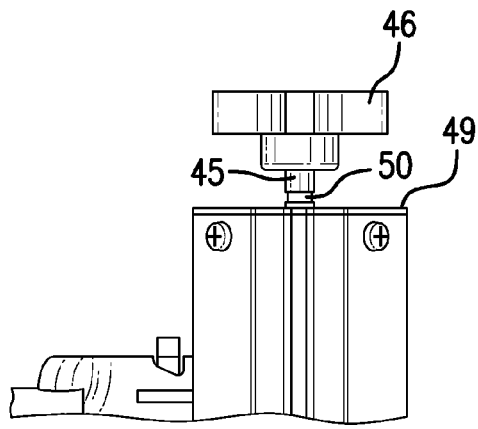
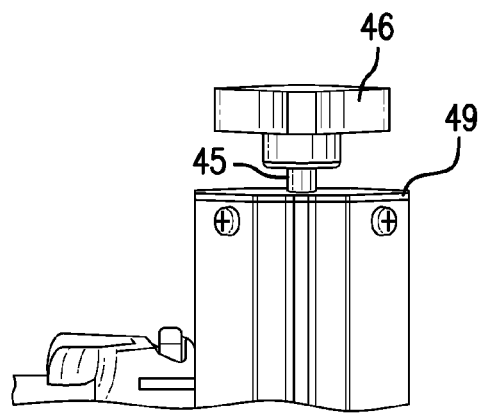
FIG.5A    FIG.5B
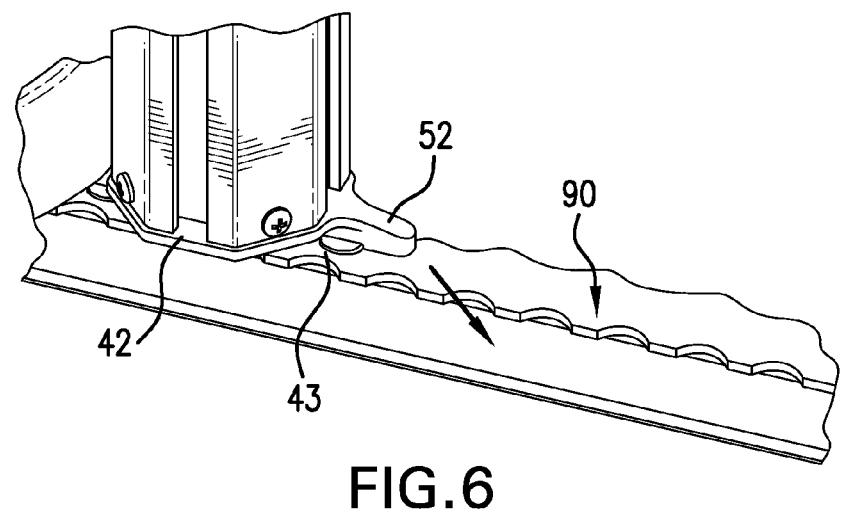
FIG.6

BOTTLE HOLDER

CROSS-REFERENCE TO RELATED APPLICATIONS

This non-provisional application claims priority to U.S. Provisional Application No. 61/660,647 filed on Jun. 15, 2012, which is incorporated herein by reference.

STATEMENT REGARDING FEDERALLY SPONSORED RESEARCH OR DEVELOPMENT

Not Applicable.

THE NAMES OF PARTIES TO A JOINT RESEARCH AGREEMENT

Not Applicable.

INCORPORATION-BY-REFERENCE OF MATERIAL SUBMITTED ON A COMPACT DISC

Not Applicable.

BACKGROUND OF THE INVENTIONS

Technical Field

The embodiments described and claimed herein relate generally to gas and liquid container securement devices. More specifically, at least some of the embodiments described herein relate to mounting or securement devices for one or more portable oxygen or other gas bottle(s), and related equipment, that are intended for use in a vehicle.

Background Art

People who have respiratory difficulties are required to transport oxygen bottles with them to ensure an adequate supply of oxygen is available during their trip. Oxygen bottles (also referred to as "cylinders"), if not properly secured in a vehicle, present obvious hazards, not only for the disabled individual, but also for the driver and other occupants. For example, the oxygen bottle, if not properly located, for example, in a transit vehicle, can present a tripping hazard for the other occupants or make it difficult to maneuver wheelchair passengers within certain vehicles. Additionally, during heavy braking, turning, or in an accident, the bottle could become a hazardous, flying projectile.

In view of these hazards, various standards have been promulgated to ensure proper securement and retention of oxygen bottles in public vehicles. See, for example, the Ambulance Manufacturers Division AMD Standard 003, "Oxygen Tank Retention System", the National School Transportation Specifications & Procedures, Support Equipment and Accessories, B.3, and the IEP-IFSP Process, Guidelines, E.11.

Conventional oxygen securement devices are typically bulky, heavy, and require the use of tools for installation and removal. The use of conventional devices proves to be cumbersome and time-consuming, especially for temporary installations. Conventional devices are heavy and voluminous and, therefore, not optimal for applications where it is necessary to use space efficiently. At least one such device is the "O2 Bus Buddy Cabinet," which is commercially available as of the date of this application. See www.o2busbuddy.com. Like other conventional securement devices, the O2 Bus Buddy suffers from several shortcomings. For example, tools are required for installation and, thus, the O2 Bus Buddy is difficult to move and becomes permanent to semi-permanent when installed. Securement of various size bottles is difficult due to its fixed space in the enclosure, and due to the straps, which only allow for limited adjustment for different height bottles as well as different diameter bottles. Additionally, the straps can be difficult to secure when there is a larger diameter bottle given the confined space of the enclosure, and must be removed from the assembly to be adjusted, then re-assembled before securing a bottle, which is very time consuming. Also, the fabricated brackets inside the O2 Bus Buddy are not adjustable or removable, and is designed to secure cylindrical objects such as oxygen bottles.

BRIEF SUMMARY OF THE INVENTIONS.

The embodiments described and claimed herein solve at least some of the problems of the conventional bottle securement devices. The present device permits no tools to be required, is light weight, minimizes bulkiness, allows flexible and temporary installation onto multiple surfaces within a vehicle, is capable of being mounted into a variety of anchorages, and adapts to be able to secure other non-tank objects such as canes, walkers, etc. Also, it is contemplated that alternate versions of the device can be adapted to be permanently mounted to the vehicle floor or wall if the user so desires.

In particular, the embodiments described herein have a compact and flexible design. They are designed to engage with floor or wall mounted anchorages (e.g. "L-Track", "L-Pocket" or "Slide 'n Click"; see www.qstraint.com/en_na/products/floor-anchor-systems) as well as fixed and/or direct floor or wall mounts. Because many transit vehicles, such as School Buses, Para-transit and ambulances, are typically provided with track that run the length of the vehicle (to secure seats and wheelchair restraints) or 'Floor Pockets' installed at various locations throughout the vehicle, the present embodiments can be mounted in numerous locations. In addition, they secure the bottles more efficiently, take up less space in the vehicle, reduce weight, can be easily removed and stored when not in use, and provide transporters the flexibility to share units between vehicles within their fleets instead of having dedicated units for each vehicle. The present embodiments also minimize potential tripping hazards, de-clutter the floor area of the vehicle and can secure more than one bottle simultaneously.

The present embodiments also have an open design, although an optional cover may be placed over the entire top of bottle and bottle holder while installed. The open design eliminates at least two steps of the O2 Bus Buddy, i.e., not having to open and close the hinged door; this reduces the number of steps and increases the speed of securing the devices, which reduces vehicle dwell times.

Furthermore, the present embodiments are "stand-alone" units. They can be mounted anywhere in the vehicle, and do not need to be placed adjacent a wall of the vehicle.

Further yet, the present embodiments are provided with a convenient and efficient secure/release device, which makes it easy to remove the device from the anchorages without the use of tools, and removal, in is a one-handed operation. In that embodiment, the locking mechanism is manipulated by a single knob located on the top of the structure. The location of the knob, at the top of the structure, also reduces injury, because it minimizes operator bending needed for installation and removal of the device from the vehicle.

At least one of the present embodiments is provided with bottle brackets that have a flexible design and are adjustable.

The bottle brackets (or holders) allow for securement of virtually all popular size oxygen bottles that are currently used in the market (e.g., at least bottle sizes from 2.5" in diameter to 5.25" in diameter). The top bottle bracket is adjustable, and can be positioned at various heights to properly enable securement of tall and short oxygen bottles. A quick release lever is provided to allow for easy and rapid adjustment of brackets to accommodate any height bottle. Bottle "straps" are used and extend from one side of the bottle brackets to the other side. The straps make securing and releasing a bottle a "one-handed" operation. At least one side of each bottle bracket is provided with an open J-hook design to allow the straps to be easily connected and released. The bottom bottle bracket is designed to support various size bottles, and keep the bottle off of the floor. As with the top bracket, the bottom bracket can be adjustable to allow the bracket to be positioned at various heights. The bottom bracket could also be provided with a quick release lever. Both the top and bottom mounting brackets contain a material that creates friction against the bottle to prevent the bottle from moving while being transported, and to prevent it from being a projectile in the event of an accident. Various materials can be used on the mounting brackets, including a neoprene rubber with a durometer of 40 A +/−5 (medium soft). A friction-inducing material is also provided on the straps. Various materials can be used on the straps, including a polyester webbing with a urethane coating (e.g., polyester webbing with urethan coating, black gloss finish produced by Bioplastics Inc., Superflex Gold Series, Part No. B1OSF100BL101-0100-A100A.

In one particular embodiment described and claimed herein, a bottle holder is provided that includes a mount, and a bottom holder and a top holder for securing a bottle. The mount includes at least one elongated channel that extends longitudinally in a vertical direction. Both the bottom holder and the top holder are secured to the mount through engagement with the channel. At least one of the top holder and the bottom holder are vertically movable along the length of the channel to multiple fixed positions.

Additional brackets or adaptors can be added to the present embodiments to secure a second bottle to the same unit, or to secure other objects including, but not limited to canes, walkers, guide dog leashes, segways, bicycles, oxygenators, regulators, unoccupied wheelchairs, cargo nets, etc. For example, a second bottom holder and top holder can be simultaneously secured to the mount through engagement with a second elongated channel Other embodiments, which include some combination of the features discussed above and below and other features which are known in the art, are contemplated as falling within the claims even if such embodiments are not specifically identified or discussed herein.

BRIEF DESCRIPTION OF THE SEVERAL VIEWS OF THE DRAWINGS.

These and other features, aspects, objects, and advantages of the embodiments described and claimed herein will become better understood upon consideration of the following detailed description, appended claims, and accompanying drawings where:

FIG. 5a is a first side view of a top portion of the assembly, showing the assembly in an unsecured configuration;

FIG. 5b is a second side view of a top portion of the assembly, showing the assembly in a secured configuration;

FIG. 6 is a second perspective view of a lower portion of the assembly;

Figure 1:
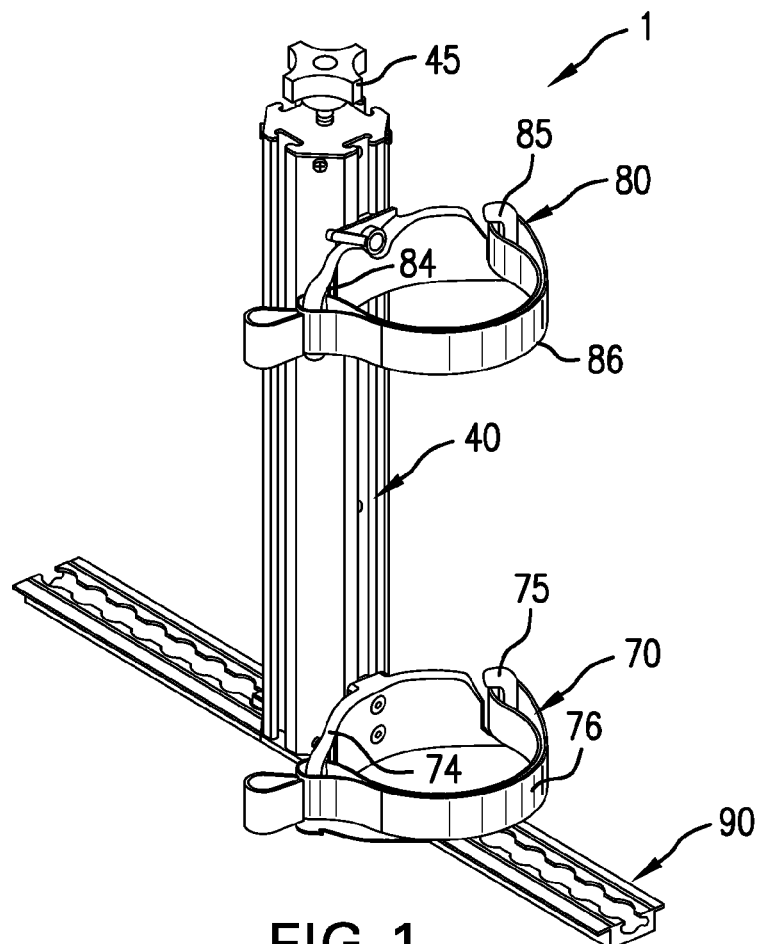
FIG. 1 is a perspective view of a first embodiment of a bottle holder assembly.

It should be understood that the drawings are not necessarily to scale and that the embodiments are sometimes illustrated by graphic symbols, phantom lines, diagrammatic representations and fragmentary views. In certain instances, details which are not necessary for an understanding of the embodiments described and claimed herein or which render other details difficult to perceive may have been omitted. It should be understood, of course, that the inventions described herein are not necessarily limited to the particular embodiments illustrated. Indeed, it is expected that persons of ordinary skill in the art may devise a number of alternative configurations that are similar and equivalent to the embodiments shown and described herein without departing from the spirit and scope of the claims.

Like reference numerals will be used to refer to like or similar parts from Figure to Figure in the following detailed description of the inventions.

DETAILED DESCRIPTION OF THE INVENTIONS

A first embodiment of a bottle holder assembly 1 is shown in FIGS. 1-9, 12a and 12b. The assembly 1, as shown, comprises a main vertical structure, or stanchion, 40, a bottom holder 70 and a top holder 80. The assembly 1 is largely manufactured from aluminum for durability and to help reduce corrosion. It is compact and light weight for ease of transportation, and is designed to weigh less than five pounds.

Figure 2:
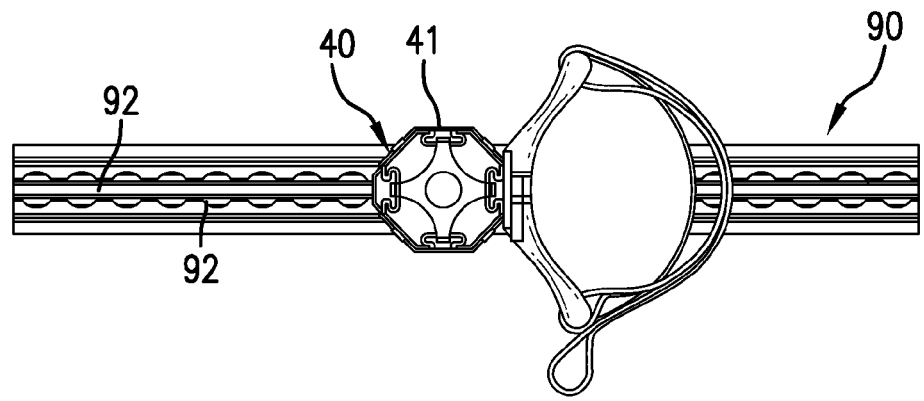
FIG. 2 is a top view of the assembly.
Figure 4:
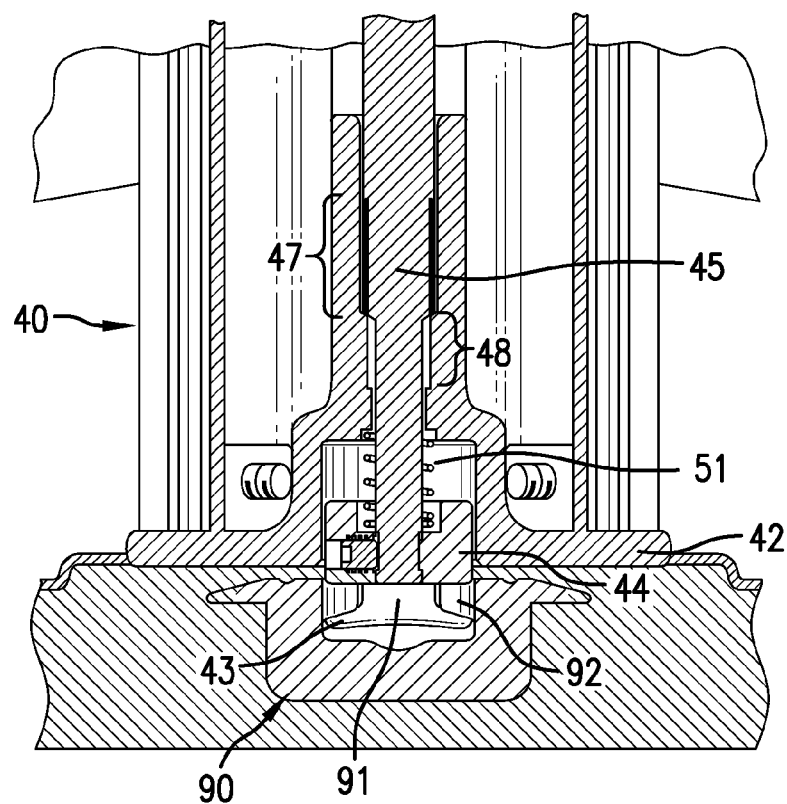
FIG. 4 is a cross-sectional view of a lower portion of the assembly.

The assembly 1 is a securement system for portable bottles (e.g., oxygen bottles) that is secured to a floor or wall-mounted fitting during its time in a vehicle. It is adjustable to accommodate multiple bottle sizes, including from 2.5" in diameter to 5.25" in diameter and sizes M2 to E. The assembly 1 prevents bottles from tipping, falling, or becoming a projectile during a sudden stop or maneuver. It is designed to safely transport medical oxygen for personal use in a variety of vehicles, including school busses, para-transit or ambulette/non-emergency medical transportation vehicles. As shown, the assembly 1 is removably secured to standard industry "L-Track" 90, which typically is installed in and runs the length of a transit vehicle, such as a municipal bus. As best shown in FIGS. 1, 2, and 4, the L-Track 90, is generally formed from extruded aluminum and provided with a C-shaped track 91 and a plurality of slots 92, uniformly spaced along the length thereof. Alternatively, the L-Track fitting 90 could be replaced with a fitting that would allow the unit to be fix mounted to the floor. Or, the L-Track fitting 90 could be replaced with another style of fitting, such as the "Slide 'n Click," manufactured and sold by Q'Straint.

One of the several benefits of the shown design is that the assembly 1 can be temporarily installed, as needed, and removed and stored when not needed, or even moved to a different vehicle. As discussed herein, the assembly 1 can be installed and removed through "one-handed" operations. No tools are required to install or remove the holder assembly to or from the L-Track 90.

As best shown in FIG. 2, a top view, the stanchion 40 has an octagonal cross-section with four channels or grooves 41 running the length of the stanchion 40, from top to bottom. The channels 41 allows mounting bracketry (such as the bottom holder 70 and the top holder 80) to be secured and positioned on four different sides of the stanchion 40. One set of mounting bracketry can be installed in a channel 41 on one side of the stanchion 40, or multiple sets of mounting bracketry can be installed in channels 41 on multiple sides of the stanchion 40.

As shown, one set of mounting bracketry (the bottom holder 70 and the top holder 80) are provided. It is contemplated that a second bottom holder (not shown) and a second top holder (not shown) could be added in the channel on the opposite side of the stanchion so as to allow the mounting of a second bottle. It is also contemplated that additional mounting bracketry could be used in other channels 41 to support, for example, walkers, canes, knapsacks, leashes for guide dogs, etc. In particular, see FIGS. 12a and 12b, where spring clips 77 are provided for holding a cane. Bracketry could also be provided that allows the assembly 1 to the mounted directly to a wall, instead of the L-Track 90, as shown. This bracketry could be engageable with and removable from the channel 41, or fixed to the assembly 1.

Figure 7:
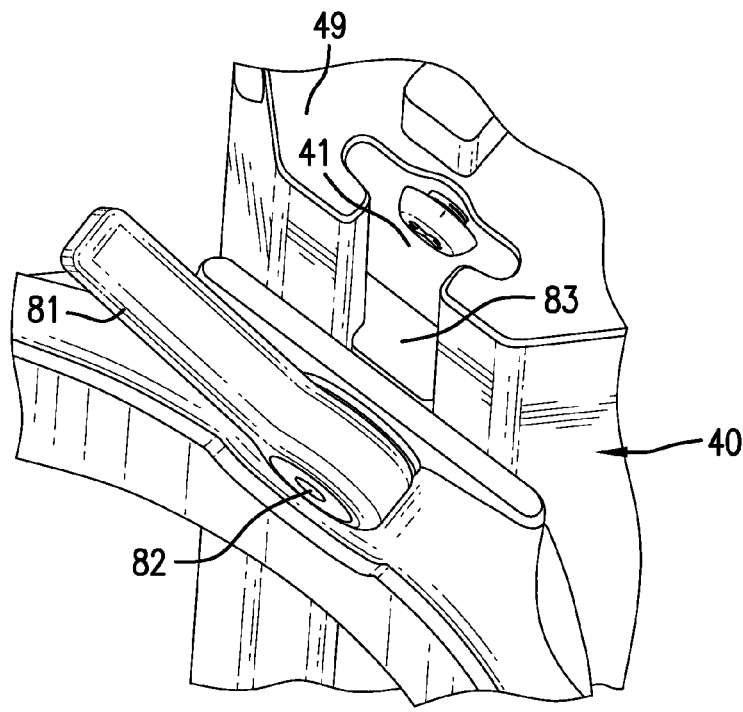
FIG. 7 is a close-up, perspective view of a portion of the top bottle holder.
Figure 8:
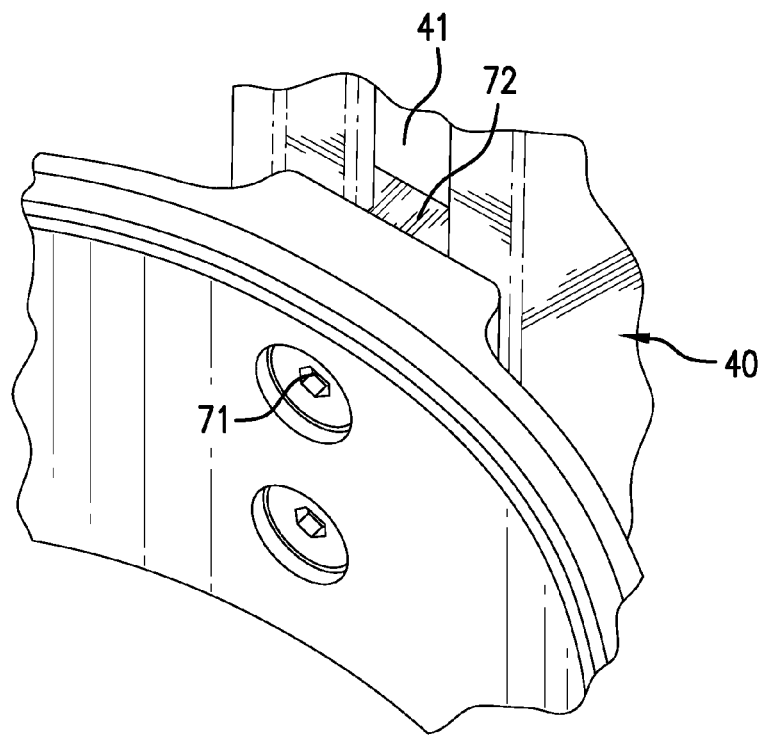
FIG. 8 is a close-up perspective view of a portion of the bottom bottle holder.

The bottom holder 70 and top holder 80 can be connected to channel 41 of the stanchion 40 using various different kinds of fasteners. As shown in FIG. 7, the top holder 80 utilizes a "quick-release" fastener that can be manipulated by hand. The quick-release fastener comprises a quick-release lever 81, a threaded bolt 82, and a nut 83. The quick release lever 81 is fixed to the threaded bolt 82. The threaded bolt 82 extends through an aperture (not shown) in the top holder 80 and engages with the nut 83, which is disposed within the channel 41. The nut 83 is provided with a special shape to correspond with the cross-section of the channel 41. Turning the lever 81 clockwise causes the threaded bolt 82 to rotate clockwise, thereby further engaging with the bolt 83 and urging the top holder 80 adjacent to the stanchion 40, such that it cannot move upward or downward along the channel 41. turning the lever 81 counter-clockwise causes the bolt 82 to rotate clockwise, thereby releasing pressure between the top holder 80 and the stanchion 40, allowing the top holder to be moved in a vertical direction, along the channel 41, to a desired position. As shown in FIG. 8, the bottom holder 70 utilizes a "fixed" fastener that requires tools to release it from the stanchion 40. In particular, two threaded bolts 71 extend through two corresponding apertures in the bottom holder to engage with two corresponding nuts 72, which are disposed within the channel. The nuts 72 is provided with a special shape to correspond with the cross-section of the channel 41.

Figure 3:
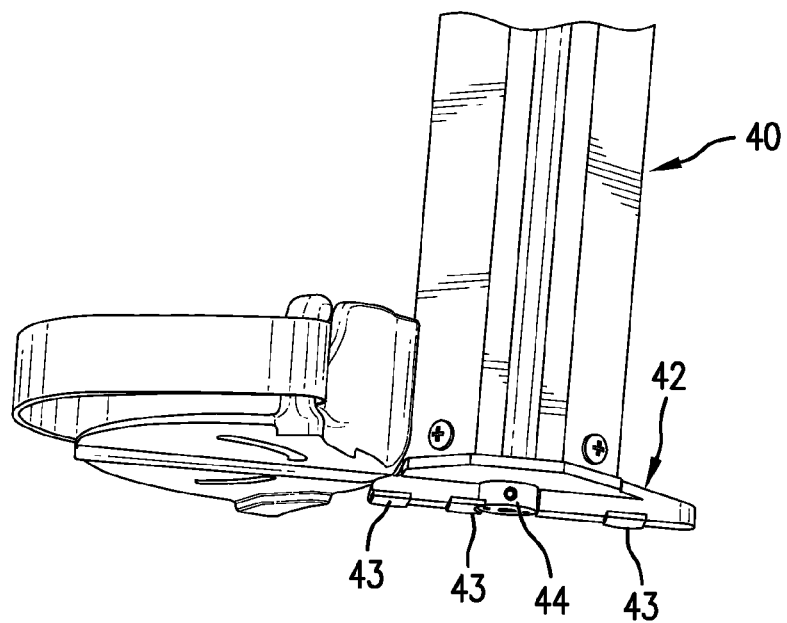
FIG. 3 is a first perspective view of a lower portion of the assembly.

As best shown in FIG. 3, the base 42 of the stanchion 40 includes features for securing the assembly in an L-Track fitting 90. In particular, the base 42 includes three pairs of outwardly extending lugs 43, which are spaced apart in various multiples of the space between adjacent slots 92 in the L-Track fitting 90. As shown, the two left pairs of lugs 43 are spaced apart the same distance as adjacent slots 92 in the L-Track fitting 90 (a multiple of 1). The two right pairs of lugs 43 are spaced apart using a multiple of 2, and the far right and far left pairs of lugs 43 are spaced apart using a multiple of 3. Because the spacing of the lugs 43 is consistent with the spacing of the slots 92, the lugs 43 can be inserted into any adjacent sets of slots 92 and slid slightly in either direction along the length of the L-Track 90, until the tops of the lugs 43 engage the underside of the C-shaped section of the track 91. The assembly 1 is semi-locked into any selected position along the length thereof by means of spring-loaded plunger 44, which is received into a selected one of the slots 92 in the L-Track 90.

The engagement of the lugs 43 with the C-shaped track 91, and the operation of the spring-loaded plunger 44, is better shown in FIG. 4. In FIG. 4, the upper surface of one pair of lugs 43 is shown engaging with the C-shaped track 91 and the plunger 44 is in a partially engaged position in a selected slot 92. The plunger 44 is connected to and manipulated by a knob 46 at the top of the stanchion by shaft 45. However, adjusters other than a knob 36 can be used, such as a toggle or lever, and connecting members other than a shaft 45 can be used, such as a cable. A short length of the shaft 45 includes a threaded portion 47 that engages with corresponding short length of threads 48 in the base 42. A spring 51 is disposed between the plunger 44 and the base 42 to urge it downward, partially into the slot 92. At this point, the threaded portion 47 of the shaft 45 is aligned, or nearly aligned, with the threads 48 of the base 42. Hand-tightening the knob 46 clockwise causes the plunger 44 to insert further into the slot 92, and thus to fully lock the assembly 1 in the L-Track 90. The plunger assembly (i.e., including the plunger 44, spring 51, shaft 45, and knob 46) is designed to allow the plunger 44 to contact the bottom of the L-Track 90 to put pressure between the upper surface of the lugs 43 and the C-shaped channel 91. This pressure will eliminate rattle. To unlock, the knob 46 is rotated counter-clockwise until the threaded portion 47 of the shaft 45 disengages with the threads 48 of the base 42, and is then pulled upward to fully disengage the plunger 44 from the slot 92. At this point, the assembly 1 can be slid lengthwise along the L-Track 90 until the lugs 43 align with corresponding slots 92, at which point the assembly 1 can be lifted from the L-Track 90 and removed.

The assembly 1 includes a visual locking indicator to help ensure the bottle is locked into place. In the shown embodiment, as best reflected in FIGS. 5a and 5b, the shaft 45 is provided with a red line 50 that is visible when the plunger 44 is not fully engaged with a slot 92 (FIG. 5a). As the knob 46 is turned clockwise, and the plunger 44 descends into the slot 92, the shaft 45 also descends into the body of the stanchion, below a top plate 49 (FIG. 5b), to indicate that the plunger 44 is fully locked.

The base 42 includes a unique feature to aide in installation of the assembly 1 into the L-Track 90. In particular, as best shown in FIG. 6, a finger or protrusion 52 is provided at one end of the base 42. During installation, it is intended that the assembly 1 be tilted slightly in the direction of the finger 52. The finger 52 is inserted first into the C-shaped track of the L-Track 90 to assist in aligning the base 42, and in particular the lugs 43, with the slots 92 of the L-Track 90.

As best shown in FIGS. 1 and 2, the top and bottom holders 80, 70 are essentially C-shaped cradles for cradling the side of a bottle (not shown). The bottom holder 70, however, includes a platform 73 for supporting the bottle from the underside (not shown). For both the top and bottom holder 80, 70, one free end of the C-shaped cradle includes an aperture 84, 74 and the opposite free end includes a hook 85, 75. Straps 86, 76 extend between the aperture 84, 74 and hook 85, 75 for holding the bottle (not shown) secure and flush against the C-shaped cradle portion of the top and bottom holders 80, 70. Each strap 86, 76 includes closed-loops at each end, one of which is looped through the aperture 84, 74 to permanently affix the strap 86, 76 to the top and bottom holders 80, 70. The strap 86 is intended to extend from the aperture 84, 74, around the bottle (not shown), through and around the hook 85, 75, returning around the bottle (not shown) adjacent to the first pass of the strap 86, 76. The free end of the strap 86, 76 is pulled tight and engages with the first pass of the strap 86, 76 using hook and loop fasteners (e.g., Velcro). The bottle (not shown) can be removed simply, and by hand, by lifting the portion of the strap 86, 76 that engages with the hook 85, 75, or by pulling the free end of the strap 86, 76 to release the hook and loop fasteners.

The strap 86, 76 comprise coated webbing that secures the bottle from both horizontal and vertical movement. The webbing is polyester with a gloss black urethane coating. The urethane coating enables the webbing to firmly grip the bottle when secured and pulled vertically.

Figure 9:
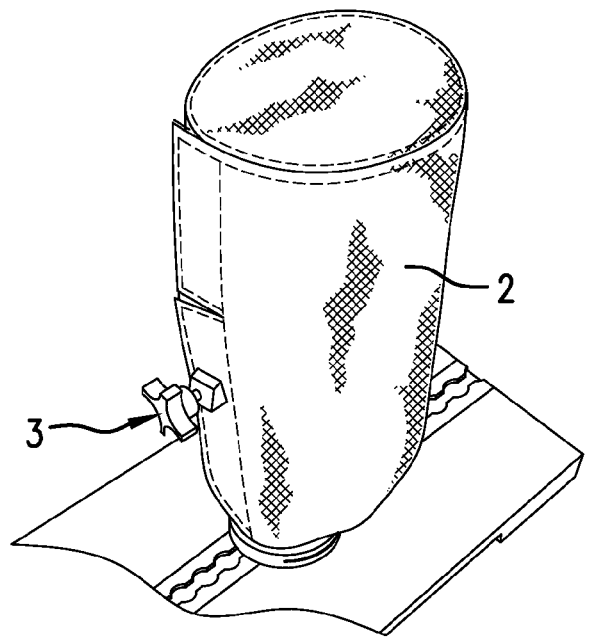
FIG. 9 is perspective view of a fully installed assembly with a cover.

As shown in FIG. 9, a padded cover 2 can be used to protect not only the bottle and associated components, but also to protect vehicle occupants from bumps and scratches.

Below are specific instructions for installing the assembly 1:

1. Align the finger (or protrusion) 82 on the base 42 of the assembly 1 and insert it into the opening running the length of the L-Track 90. The knob 86 on top of assembly should be turned fully in the counter-clockwise direction and pulled upward.

2. After the entire base 42 is inserted fully into the track, the knob 86 on the top of the assembly 1 can be released which will allowing plunger 44 to move down into default position via the spring 51 force. Move the assembly 1 in the track until the plunger 44 engages into adjacent hole or slot 92 in the L-Track 90, eliminating horizontal movement.

3. Rotate the knob 46 on top of the stanchion 40 clockwise until tight. This will tighten the assembly 1 to the L-Track 90, reducing any additional movement of the assembly 1.

4. Make sure hook and loop straps 86, 76 are removed from one side of top and bottom holders 80, 70. Place bottle (not shown) on platform 73 of bottom holder 70. The back surface of the bottle (not shown) should be resting against the cradles of both the top and bottom holders 80, 70.

5. Pull straps 86, 76 on bottom holder 70 and top holder 80 around front surface of bottle and through slot and then securely pull to ensure there is a tight engagement then mate hook and loop fasteners on strap 86, 76 together ensuring secured attachment.

6. Place cover 2 over top and around bottle/regulator (not shown) and assembly 1. Open or close appropriate flaps as required to allow clearance for knobs 3 or oxygen lines.

Below are specific instructions for removing the assembly 1:

1. Remove cover 2 from top of assembly 1.

2. Undo both top and bottom hook and loop straps 86, 76 that are securing bottle (not shown).

3. Lift bottle (not shown) upward and remove from assembly 1.

4. Rotate knob 46 on top of stanchion 40 counter-clockwise. Shaft 45 will become disengaged from threads 48. After shaft 45 is disengaged from threads 48, knob 46 can be lifted upward. (Red Line 50 on shaft 45 directly below knob 46 will be visible.)

5. While lifting knob 46 (and thus plunger 44) in upward position, slide assembly 1 in track. Firmly lift upward and assembly 1 will disengage from L-Track when lugs 43 are aligned with slots 92.

Figure 10:
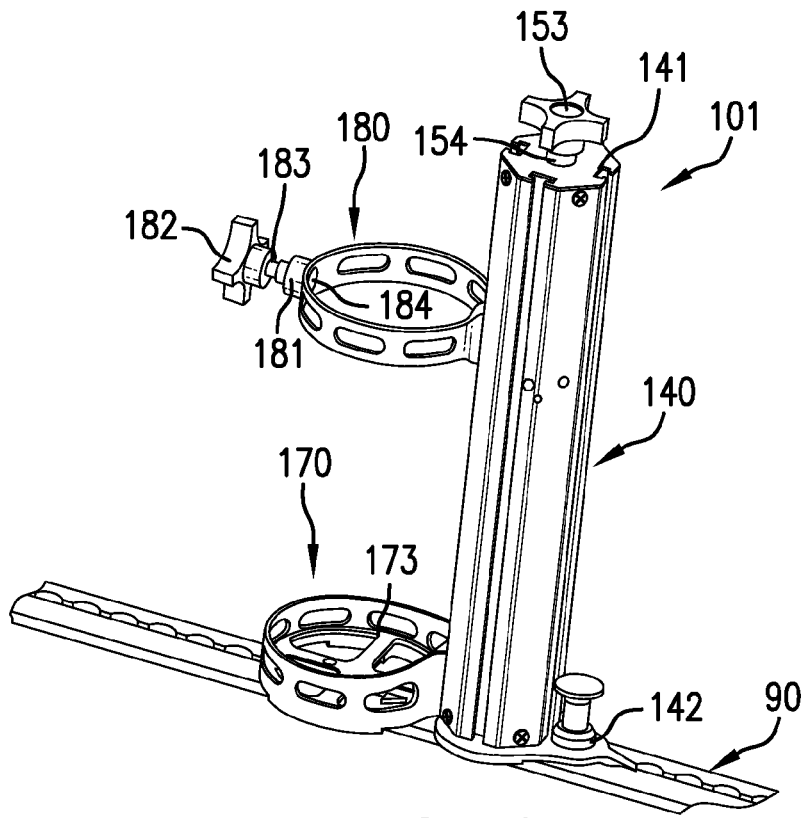
FIG. 10 is a perspective view of a second embodiment of a bottle holder assembly.
Figure 11:
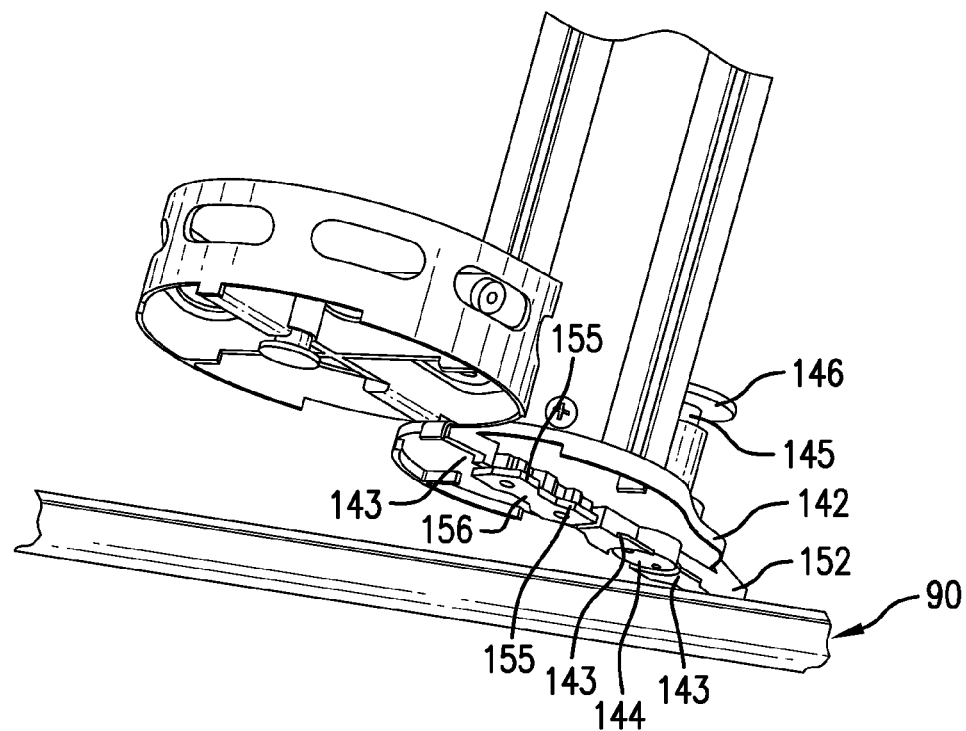
FIG. 11 is perspective view of a lower portion of the assembly.
Figures 12A, 12B:
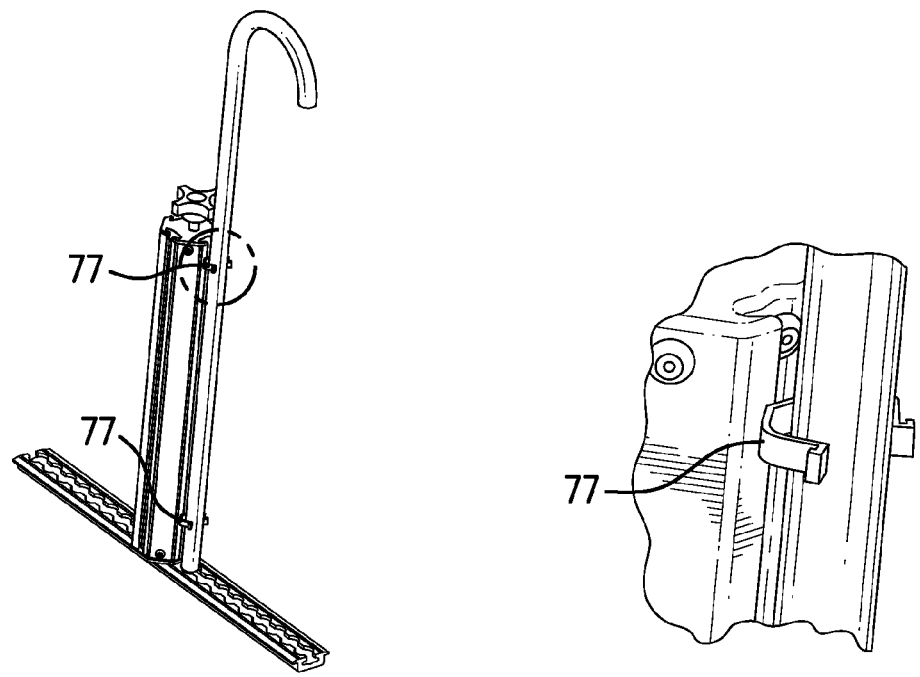
FIG. 12a is a perspective view of the first embodiment of the bottle holder assembly with alternative brackets for holding a cane.
FIG. 12b is a detail view of the alternative bracket.

A second embodiment of an bottle holder assembly 101 is shown in FIGS. 10-11. The assembly 101, as shown, like the first embodiment, comprises a main vertical structure, or stanchion, 140, a bottom holder 170 and a top holder 180. The assembly 101 is largely manufactured from aluminum for durability and to help reduce corrosion. It is compact and light weight for ease of transportation, and is designed to weigh less than five pounds.

The assembly 101 is a securement system for portable bottles that is secured to a floor or wall-mounted fitting during its time in a vehicle. The assembly 101 prevents bottles from tipping, falling, or becoming a projectile during a sudden stop or maneuver. It is designed to safely transport medical oxygen for personal use in a variety of vehicles, including school busses, para-transit or ambulette/non-emergency medical transportation vehicles. As shown, and as with the first embodiment, the assembly 101 is removably secured to standard industry "L-Track" 90, which typically is installed in and runs the length of a transit vehicle, such as a municipal bus. As best shown in FIGS. 1, 2, and 4, the L-Track 90, is generally formed from extruded aluminum and provided with a C-shaped track 91 and a plurality of slots 92, uniformly spaced along the length thereof. Alternatively, the L-Track fitting 90 could be replaced with a fitting that would allow the unit to be fix mounted to the floor. Or, the L-Track fitting 90 could be replaced with another style of fitting, such as the "Slide 'n Click," manufactured and sold by Q'Straint.

Referring again to FIGS. 10-11, one of the several benefits of the shown design is that the assembly 101 can be temporarily installed, as needed, and removed and stored when not needed, or even moved to a different vehicle. As discussed herein, no tools are required to install or remove the assembly 101 to or from the L-Track 90.

With exception of the base 142, the stanchion 140 is largely constructed in accordance with the stanchion 40 of the first embodiment. Indeed, the stanchion 140 has an octagonal cross-section with four channels or grooves 141 running the length of the stanchion 140, from top to bottom. The channels 141 allow mounting bracketry (such as the bottom holder 170 and the top holder 180) to be secured and positioned on four different sides of the stanchion 140. One set of mounting bracketry can be installed in a channel 141 on one side of the stanchion 140, or multiple sets of mounting bracketry can be installed in channels 141 on multiple sides of the stanchion 140.

As shown, one set of mounting bracketry (the bottom holder 170 and the top holder 180) are provided. It is contemplated that a second bottom holder (not shown) and a second top holder (not shown) could be added in the channel on the opposite side of the stanchion 140 so as to allow the mounting of a second bottle. It is also contemplated that additional mounting bracketry could be used in other channels 141 to support, for example, walkers, canes, knapsacks, leashes for guide dogs, etc. Bracketry could also be provided that allows the assembly 101 to the mounted directly to a wall, instead of the L-Track 90, as shown. This bracketry could be engageable with and removable from the channel 141, or fixed to the assembly 101.

The bottom holder 170 and top holder 180 can be connected to channel 141 of the stanchion 140 using various different kinds of fasteners. In the particular embodiment shown, the bottom holder 170 and top holder 180 utilize the same fasteners and fastener configuration as the bottom holder 70 of the first embodiment, as described in detail above. It is contemplated, however, that the "quick-release faster" used with the top holder 80 of the first embodiment could also be used with one or both of the bottom holder 170 and top holder 180.

As best shown in FIG. 11, the base 142 of the stanchion 140 includes features for securing the assembly 101 in an L-Track fitting 90. In particular, the base 142 includes three pairs of outwardly extending lugs 143. The base 142 also includes a moveable retainer 156, that is connected to knob 153 at the top of the stanchion 140 by a threaded shaft 154. The movable retainer 156 includes two pairs of spaced lugs 155. The lugs 143, 155 are spaced apart in various multiples of the space between adjacent slots 92 in the L-Track fitting 90. Because the spacing of the lugs 143, 155 is consistent with the spacing of the slots 92, the lugs 143, 155 can be inserted into any adjacent sets of slots 92 and slid slightly in either direction along the length of the L-Track 90, until the tops of the lugs 143 engage the underside of the C-shaped section of the track 91. The assembly 101 is semi-locked into any selected position along the length thereof by means of spring-loaded plunger 144, which is received into a selected one of the slots 92 in the L-Track 90. The plunger 144 is connected to a pull-knob 146 at the top of the base 142 by shaft 145. A spring (not shown) is disposed between the plunger 144 and the base 142 to urge it downward, partially into the slot 92.

Hand-tightening the knob 153 clockwise causes the retainer 156 to move vertically downward until it contacts the bottom of the L-Track 90, putting pressure between the upper surface of the lugs 43 and the C-shaped channel 91. This pressure will eliminate or reduce rattle and fully lock the assembly 101 to the L-Track 90. To unlock, the knob 153 is rotated counter-clockwise to release the pressure. The pull-knob 146 is then held in a lifted position. At this point, the assembly 101 can be slid lengthwise along the L-Track 90 until the lugs 143 align with corresponding slots 92, at which point the assembly 101 can be lifted from the L-Track 90 and removed.

As with the first embodiment (see FIGS. 5a and 5b), the assembly 101 includes a visual locking indicator, such as a red line on the shaft 154, to help ensure the bottle is locked into place. Also like the first embodiment, the base 142 includes a finger or projection 152 to aide in installation of the assembly 101 into the L-Track 90.

As best shown in FIG. 10, the top and bottom holders 180, 170 are rings for surrounding a bottle (not shown). The bottom holder 170, however, includes a platform 173 for supporting the bottle from the underside (not shown). The top holder 180 includes threaded aperture 181. A knob 182 with a threaded stem 183 extends through and engages the aperture 181. A bottle engagement member 184 is provided at the end of the stem 183. When the knob 182 is turned clockwise, the threaded stem 183 extends into the inside of the ring, and the bottle engagement member 184 engages with the bottle (not shown) to secure the bottle tightly to the assembly 101. When knob 182 is tightened, all side to side movement of the bottle (not shown) is restricted.

As best shown in FIG. 11, an additional set of lugs 171 are provided on the underside of the platform. These lugs 171 are configured to engage with the L-Track 90 to provide additional stability.

The assembly 101 can be provided with a padded cover 2, similar to the first embodiment (see FIG. 9).

Below are specific instructions for installing the assembly 101:

1. Align the finger or protrusion 152 on the base 142 of the assembly 101 and insert it into the opening running the length of the L-Track 90. The knob 153 on top of stanchion 140 should be turned fully in the counter-clockwise direction before insertion.

2. After the entire base 142 is inserted fully into the L-Track 90, move assembly in the track until the plunger 144 engages into adjacent hole or slot 92 in the L-Track 90, eliminating horizontal movement.

3. Rotate the knob 153 on top of the main structure clockwise until tight. This will tighten the assembly 101 to the L-Track 90, reducing any additional movement of the structure.

4. Insert the bottle (not shown) through the hole in the top ring (top holder) 180 and seat the bottle (not shown) onto the bottom holder 170.

5. Rotate the knob 182 on the top holder 180 which forces the bottle engagement member 184 against the bottle (not shown) and eliminates any movement of the bottle (not shown).

6. Place cover 2 over top and around bottle/regulator (not shown) and assembly 101. Open or close appropriate flaps as required to allow clearance for knob 3 or oxygen lines (not shown).

Below are specific instructions for removing the assembly 101:

1. Remove cover 2 from top of assembly 101.

2. Loosen knob 182 on top holder 180 which relieves pressure on bottle (not shown).

3. Lift bottle (not shown) upward and remove from assembly 101.

4. Rotate knob 153 on top of stanchion 140 counter-clockwise until resistance is felt.

5. Lift pull-knob 156 on base 142 of stanchion 140 and slide assembly 101 in L-Track 90 while firmly lifting upward and assembly 101 will disengage from L-Track 90 at next opening or slot 92.

Figure 13:
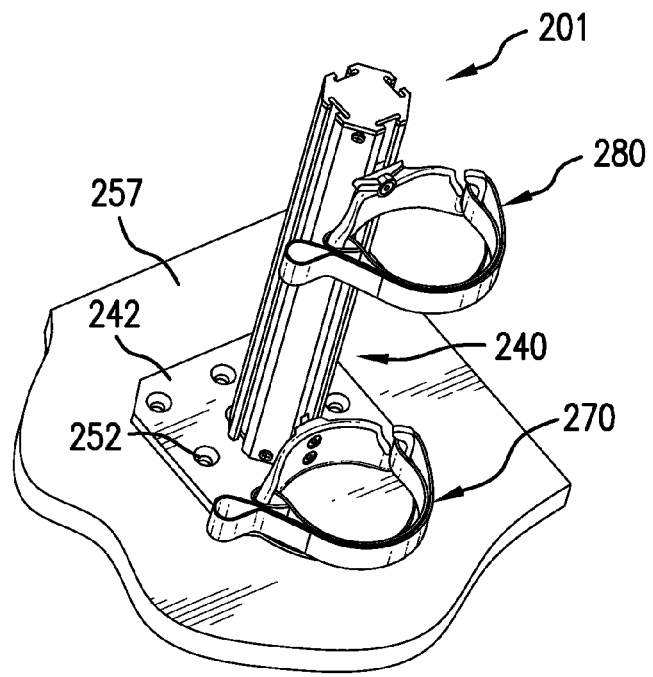
FIG. 13 is a third embodiment of the bottle holder assembly which is designed for direct mounting to the floor of a vehicle; and, FIG. 14 is a fourth embodiment of the bottle holder assembly which is designed for direct mounting to the wall, or other vertical service, of a vehicle.

A third embodiment of a bottle holder assembly 201 is shown in FIG. 13. The assembly 201, as shown, like the first embodiment, comprises a main vertical structure, or stanchion, 240, a bottom holder 270 and a top holder 280. The bottom holder 270 and top holder 280 are identical to the bottom holder 70 and top holder 80 of the first embodiment. The stanchion 240 is largely identical to the stanchion 40 of the first embodiment; however, unlike the first embodiment, the assembly 201 is designed for permanent/semi-permanent mounting directly to the floor or other horizontal surface 257 of a vehicle (not shown). The stanchion 240 is therefore provided with a different base 242 than the first embodiment, and lacks the internal and external moving structures (e.g., the shaft 45, knob 46, plunger 44, spring 51, etc.). The base 242, as shown, comprises a plurality of countersink bores 252 through which fasteners (not shown) can fasten the base 242 to a horizontal surface 257 of a vehicle (not shown).

Figure 14:
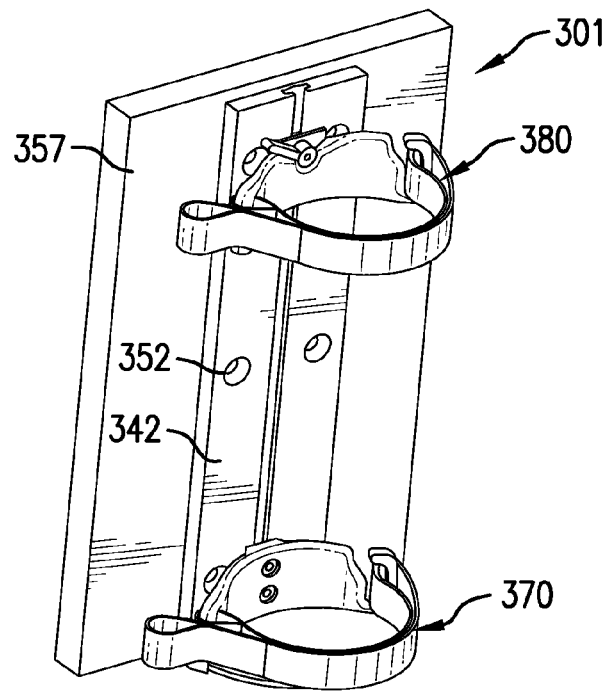

A fourth embodiment of a bottle holder assembly 301 is shown in FIG. 14. The assembly 301 is designed for permanent/semi-permanent mounting directly to the wall or other vertical surface 357 of a vehicle (not shown). The assembly 401 includes a mount 342, a bottle holder 370 and a top holder 380. The bottom holder 370 and the top holder 380 are identical to the bottom holder 70 and top holder 80 of the first embodiment. The mount 370 is shown as including a single groove 341 running the length of the mount, from top to bottom, although it is contemplated that the mount 370 could include multiple grooves (not shown). The channel 341 is essentially identical to the channels 41 of the first embodiment in that it allows mounting bracketry (such as the bottom holder 370 and the top holder 380) to be secured and vertically positioned to accommodate different height and diameter bottles (not shown). The mount 370 also includes a plurality of countersink bores 252 through which fasteners (not shown) can fasten the mount 370 to a vertical surface 357 of a vehicle (not shown).

Although the inventions described and claimed herein have been described in considerable detail with reference to certain embodiments, one skilled in the art will appreciate that the inventions described and claimed herein can be practiced by other than those embodiments, which have been presented for purposes of illustration and not of limitation. Therefore, the spirit and scope of the appended claims should not be limited to the description of the embodiments contained herein.

We claim:

1. A bottle holder comprising:
a mount, a bottom holder and a top holder for securing a bottle, an adjuster, and a connecting member;
the mount including at least one elongated channel, the channel extending longitudinally in a vertical direction;
the bottom holder being secured to the mount through engagement with the channel;
the top holder being secured to the mount through engagement with the channel;
at least one of the top holder and the bottom holder being vertically movable along the length of the channel to multiple fixed positions;
the mount comprising a stanchion and the channel extending along at least a portion of a height of the stanchion, wherein the mount is supported on a base, the base comprising a track fitting for engaging with a track anchorage, the base including at least one track engaging lug and at least one plunger, the plunger being movable between an extended position and a retracted position, the plunger in the retracted position allowing insertion and translation of the lug in a track, the plunger in the extended position being such that a portion of the plunger is in registration with an opening in the track to restrict translation of the base along the track and restrict removal of the base from the track; and,
the adjuster being disposed at a top of the stanchion and the connecting member being connected at one end to the adjuster, extending through the stanchion, and connected at the opposite end to the plunger, the connecting member being adapted to move the plunger between its extended and retracted positions.

2. The bottle holder of claim 1, wherein the track anchorage is configured to be fixed to a horizontal surface.

3. The bottle holder of claim 1, wherein the mount comprises a stanchion and the channel extends along at least a portion of a height of the stanchion.

4. The bottle holder of claim 3, wherein the at least one elongated channel comprises a plurality of elongated channels disposed about a periphery of the stanchion, each elongated channel being configured to receive a holders for securing a separate object.

5. The bottle holder of claim 1, wherein at least one of the top holder and the bottom holder is vertically movable along the length of the channel without the use of tools.

6. The bottle holder of claim 1, wherein the connecting member is a shaft adapted to both translate vertically within the stanchion and rotate.

7. The bottle holder of claim 6 further comprising a spring urging the plunger downward away from the base, and into partial engagement with the track, whereby pulling the knob upward retracts the plunger from the track.

8. The bottle holder of claim 7, wherein the shaft includes a threaded portion that is releasably engagable with a corresponding threaded portion of the bottle holder, allowing manipulation of the plunger through at least one movement including rotation and vertical displacement of the shaft.

9. The bottle holder of claim 1 further comprising a quick-disconnect toggle for at least one of the top holder and the bottom holder wherein the toggle can be manipulated using a single hand and is for securing at least one of the top holder and the bottom holder to the channel.

10. The bottle holder of claim 1, wherein at least one of the top holder and bottom holder comprise high friction material to grip the bottle.

11. The bottle holder of claim 1, wherein the top holder and bottom holder each comprise a support and a strap, the support having a first end and a second, opposite end, the strap being connected to the first end and connected to the second end.

12. The bottle holder of claim 11, wherein the strap of at least one of the top holder and the bottom holder is a continuous member having a first portion that engages and extends from the first end of the support to the second end of the support and a second portion that extends from the second end of the support toward the first end and connects to the first portion of the strap via hook and loop fasteners.

13. The bottle holder of claim 12 wherein the second end of the support of at least one of the top holder and the bottom holder comprises a hook to allow the strap to be releasably connected and removed by hand.

14. The bottle holder of claim 11, wherein the strap comprises high friction material to grip the bottle.

15. The bottle holder of claim 1, wherein the bottom holder includes a platform for supporting a bottom of the bottle.

16. The bottle holder of claim 1, further comprising a hand-releasable fitting for securing the bottle holder to an anchorage.

17. The bottle holder of claim 16, wherein the anchorage track is an elongated track that is fixed to at least one surface of the vehicle.

18. A bottle holder comprising:
a mount, and a bottom holder and a top holder for securing a bottle;
the mount including at least one elongated channel, the channel extending longitudinally in a vertical direction;
the bottom holder being secured to the mount through engagement with the channel;
the top holder being secured to the mount through engagement with the channel:
at least one of the top holder and the bottom holder being vertically movable along the length of the channel to multiple fixed positions;

the mount comprising a stanchion and the channel extending along at least a portion of a height of the stanchion, wherein the mount is supported on a base, the base comprising a track fitting for engaging with a track anchorage, the base including at least one track engaging lug and at least one plunger, the plunger being movable between an extended position and a retracted position, the plunger in the retracted position allowing insertion and translation of the lug in a track, the plunger in the extended position being such that a portion of the plunger is in registration with an opening in the track to restrict translation of the base along the track and restrict removal of the base from the track; and, wherein the plunger, in its extended position, is urged against the bottom of the track.

* * * * *